US00PP27282P3

(12) United States Plant Patent
Olesen et al.

(10) Patent No.: US PP27,282 P3
(45) Date of Patent: Oct. 18, 2016

(54) ***CLEMATIS* PLANT NAMED 'EVIPO054'**

(50) Latin Name: *Clematis viticella*
Varietal Denomination: Evipo054

(71) Applicants: Mogens Nyegaard Olesen, Fredensborg (DK); Raymond J. Evison, St. Sampsons (GB)

(72) Inventors: Mogens Nyegaard Olesen, Fredensborg (DK); Raymond J. Evison, St. Sampsons (GB)

(73) Assignee: Poulsen Roser A/S, Fredensborg (DK)

( * ) Notice: Subject to any disclaimer, the term of this patent is extended or adjusted under 35 U.S.C. 154(b) by 17 days.

(21) Appl. No.: 14/121,280

(22) Filed: Aug. 15, 2014

(65) Prior Publication Data

US 2016/0050831 P1 Feb. 18, 2016

(51) Int. Cl.
*A01H 5/02* (2006.01)

(52) U.S. Cl.
USPC ..... Plt./228

(58) Field of Classification Search
USPC ..... Plt./228
See application file for complete search history.

(56) References Cited

PUBLICATIONS

Retrieved Feb. 17, 2016 from the website de.poulsenroses.eu/sortiment/rosencollectionen/boulevard/manon.aspx (1 pg total).*
"Perfection by Poulsen—*Clematis* Main Varieties 2013" (3 pgs total).*

* cited by examiner

*Primary Examiner* — Susan McCormick Ewoldt

(57) ABSTRACT

A new *Clematis* plant with a compact growth habit, profuse, violet flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

3 Drawing Sheets

Botanical classification:
Genus: *Clematis.*
Species: *viticella.*
Variety denomination: 'Evipo054'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling The two parents were crossed during the summer of 2003 and the resulting seeds were planted the following winter in a controlled environment in Guernsey, Channel Islands, United Kingdom. The new variety named 'Evipo054' originated as a single seedling from the stated cross.

The new *clematis* plant may be distinguished from its female seed parent and male pollen parent by the following characteristics. The seed parent has light pink flowers while the claimed plant has violet flowers. The pollen parent has white anthers while the new variety has purple anthers.

The objective of the hybridization of this *clematis* plant was to create a new and distinct variety for nursery culture with unique qualities such as:

1. Uniform and abundant violet flowers;
2. Vigorous and compact growth, making the variety suitable for container culture; and
3. Improved disease resistance.

This combination of qualities was lacking in *clematis* plants that were in commercial cultivation and the qualities have been substantially achieved in the new variety.

'Evipo054' was selected by Mogens N. Olesen and Raymond J. Evison in their *clematis* development program in the Channel Islands, United Kingdom in 2004. Asexual reproduction of 'Evipo054' by means of vegetative cuttings and traditional layering was first performed by Mogens N. Olesen and Raymond J. Evison in the nursery during the summer of 2004. This initial and subsequent asexual propagations have demonstrated that the characteristics of 'Evipo054' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo054'.

Specifically illustrated in FIG. 1 are flower buds appearing on a flowering branch, open flowers on the branch, tepals detached, detached reproductive flower parts, and a seed head.

DETAILED DESCRIPTION OF THE VARIETY

Figure 1:
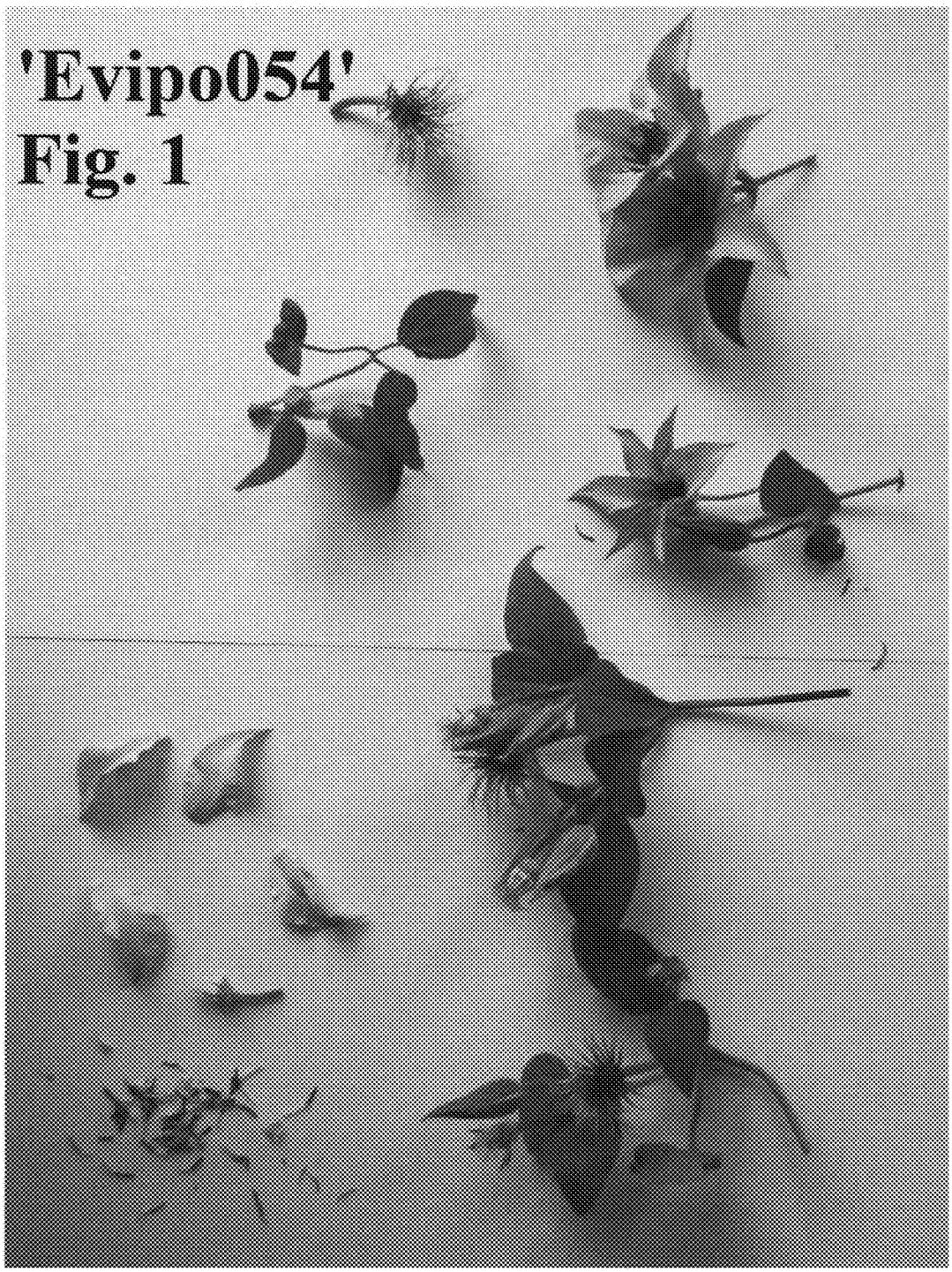
Figure 2:
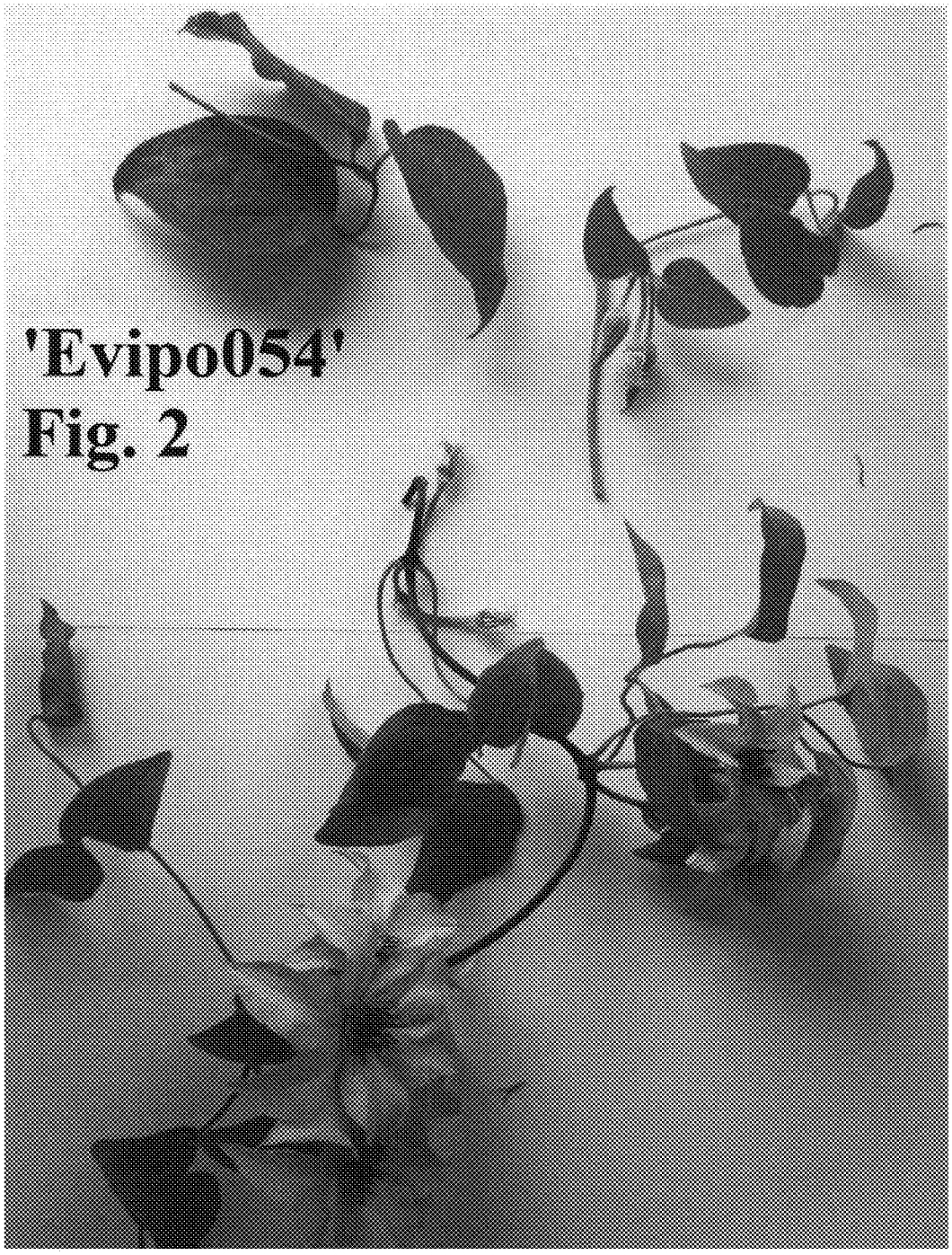
FIG. 2 shows an entire flowering branch as well as leaves.
Figure 3:
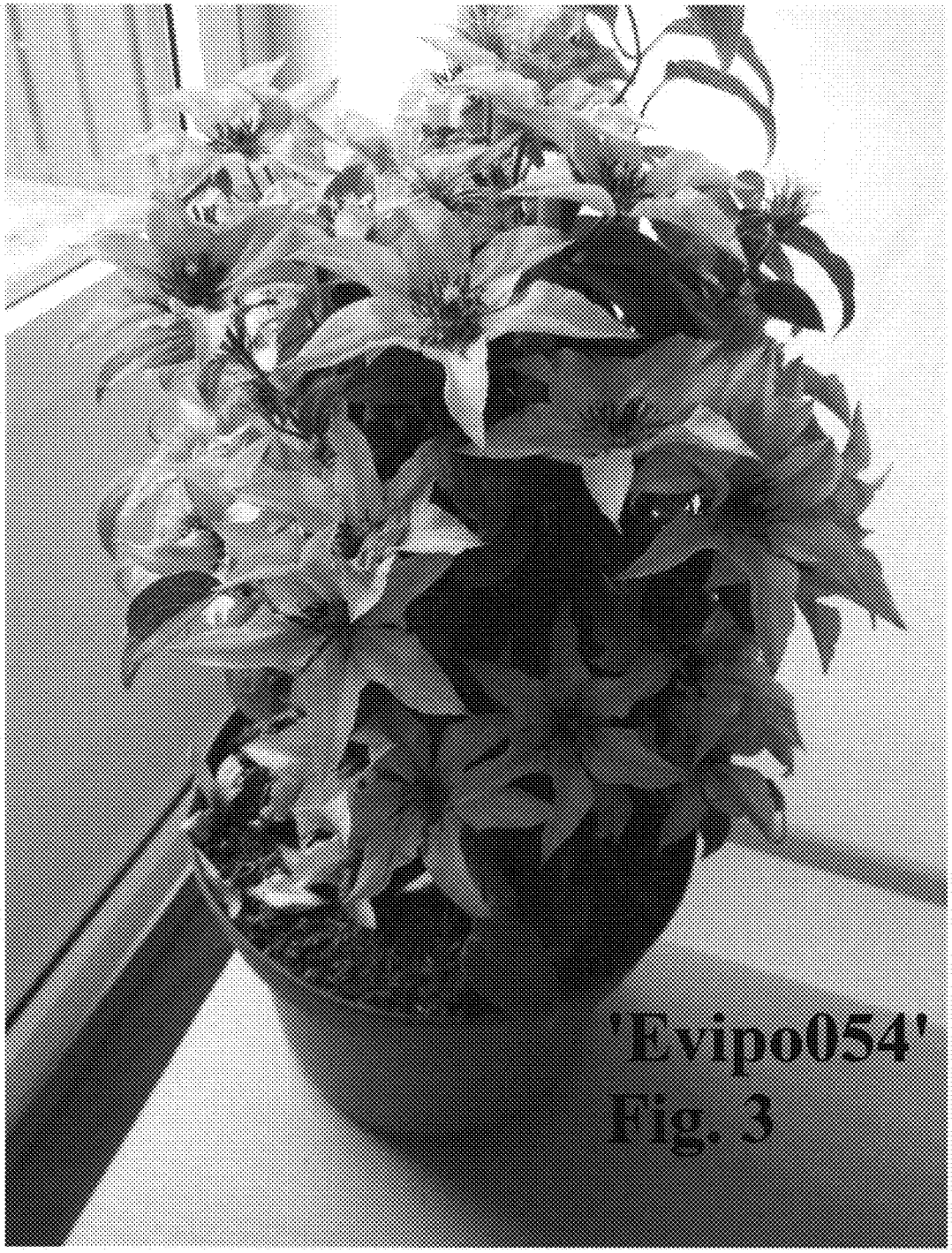
FIG. 3 shows a specimen of the new variety flowering in a container. Plants shown are 2 years of age.

The following is a detailed description of 'Evipo054', as observed in its growth throughout the flowering period in Odense Denmark. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety 'Poulvo', non-patented, are compared to 'Evipo054'in Chart 1.

CHART 1

| | 'Evipo054' | 'Poulvo' |
|---|---|---|
| Flower bud form | Sagittate | Ovate |
| Tepal upper surface after opening | Violet Group 84C. | Red-Purple Group 71A. |
| Tepal count | 6 | 6 - 8 |

FLOWER AND FLOWER BUD

Blooming habit: Recurrent. The natural flowering period is generally from May to September.

Flower bud:
- *Size*.—Normally 25 mm in length. Bud diameter is 8 mm.
- *Bud form*.—Sagittate.
- *Bud color*.—At ¼ opening tepals are Purple-Violet Group N82C.

Peduncle:
- *Surface texture*.—Lightly pubescent.
- *Length*.—18-35 mm.
- *Color*.—Yellow-Green Group 146D with intonations of Greyed-Purple Group 184A.
- *Strength*.—Moderately strong.

Receptacle:
- *Surface texture*.—Smooth.
- *Shape*.—Broad funnel.
- *Size*.—1 mm (h)×3 mm (w).
- *Color*.—Yellow-Green Group 144D.

Flower arrangement:
- *Location on vine*.—New growth only.
- *Borne*.—Flower buds develop in clusters of 3 to 7.

Flower bloom:
- *Size*.—On average, flowers are 85 mm in diameter and 15 mm in depth.
- *Profile*.—Flat to somewhat convex.
- *Fragrance*.—Light.
- *Lasting quality*.—Flowers normally remain up to 10 days on the plant.
- *Attitude*.—Flower attitude is mostly upwards and partially outwards.

Tepals:
- *Tepal color*.—Upon opening, the upper surface is Violet Group 84B. The lower surface is Violet Group 84A. After opening, the upper surface is Violet Group 84C. The lower surface is Violet Group 84D.
- *Quantity*.—Normally 6 tepals.
- *Size*.—About 45 mm in length by 25 mm wide.
- *Shape*.—Individual tepal shape is lanceolate. The tepal apex is acuminate. The tepal base is typically acute.
- *Apex recurvature*.—Recurved.
- *Tepal cross section*.—Cupped.
- *Margins*.—Entire.
- *Persistence*.—Tepals drop off cleanly.
- *Tepal overlap*.—Partial.

Reproductive organs:
- *Arrangement*.—Moderately compact.
- *Pollen*.—None observed.
- *Anthers*.—Size: 4 mm in length. Color: Greyed-Purple Group 187B. Quantity: On average, 40.
- *Filaments*.—Color: Green-Yellow Group 1B. Length: 2-6 mm.
- *Pistils*.—Quantity: On average, 40.
- *Stigmas*.—Superior in location relative to the length of the filaments and the height of the anthers.
- *Styles*.—Color: Green-Yellow Group 1B. Length: 8 mm.
- *Seed head characteristics*.—Size: 20 mm in height. 40 mm in diameter. Quantity: The average number of seeds produced per seed head is 40.
- *Style appearance*.—Plumose, semi-erect.

PLANT

Plant form: Climbing.

Plant growth: Moderately vigorous.

Size: Seasons growth attains 100 to 150 cm in height. Average spread is 50 cm.

Stems:
- *Color*.—Juvenile stems are Yellow-Green Group 144B. Mature stems are Brown Group 200B.
- *Internodes*.—On average, 10 cm between nodes.
- *Length*.—Normally 50 cm from the base of the plant to the flowering portion of the stem.
- *Diameter*.—Normally 2-3 mm.
- *Texture*.—Mature stems are ribbed.

Plant foliage:
- *Leaf characteristics*.—Deciduous.
- *Arrangement*.—Trifoliate.
- *Leaf size*.—Compound leaves are normally 100 to 150 mm (l)×120 to 150 mm (w). Leaflets are normally 50 to 70 mm (l)×30 to 50 mm (w).
- *Abundance*.—On average 2 leaves per 10 cm of stem.
- *Leaf color*.—Juvenile upper Yellow-Green Group 146B. Juvenile lower Yellow-Green Group 147C. Mature upper Yellow-Green Group 147A. Mature lower Yellow-Green Group 147B.
- *Stipules*.—Absent.
- *Petioles*.—Size: Normally 35 to 45 mm in length by 2 mm diameter. Texture: Smooth. Color: Yellow-Green Group 146D with some intonations of Greyed-Red Group 177A.
- *Petiolule*.—Size: Normally 10 to 25 mm in length by 2 mm diameter. Texture: Smooth. Color: Yellow-Green Group 146B with some intonations of Greyed-Red Group 177A.
- *Leaflet shape*.—Generally elliptic.
- *Margin*.—Entire.
- *Surface*.—The upper side is smooth. The lower side is smooth.
- *Thickness*.—Moderate.
- *Glossiness*.—Not glossy.

Disease resistance: Subject to any disease that normally attacks the species. However the variety is more tolerant to *clematis* wilt, *Ascochyta clematidina*, than some *clematis* known to the inventors.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *clematis* plant named 'Evipo054', substantially as described and illustrated, due to its abundant violet flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

'Evipo054'

'Evipo054'